US00PP17887P2

(12) United States Plant Patent
Strode

(10) Patent No.: US PP17,887 P2
(45) Date of Patent: Jul. 31, 2007

(54) ***COLOCASIA* PLANT NAMED 'MIDNIGHT'**

(50) Latin Name: *Colocasia esculenta*
Varietal Denomination: Midnight

(75) Inventor: Randall E. Strode, Longwood, FL (US)

(73) Assignee: Agri-Starts, Inc., Apopka, FL (US)

( * ) Notice: Subject to any disclaimer, the term of this patent is extended or adjusted under 35 U.S.C. 154(b) by 0 days.

(21) Appl. No.: 11/351,847

(22) Filed: Feb. 10, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Colocasia* plant named 'Midnight', characterized by its tall and upright plant form; relatively slow growth rate; and uniformly black-colored leaves.

1 Drawing Sheet

Botanical designation: *Colocasia esculenta.*
Cultivar denomination: 'Midnight'.

BACKGROUND OF THE INVENTION

The present Invention relates to a new and distinct cultivar of *Colocasia* plant, botanically known as *Colocasia esculenta* and hereinafter referred to by the name 'Midnight'.

The new *Colocasia* is a naturally-occurring branch mutation of an unnamed selection of *Colocasia esculenta,* not patented. The new *Colocasia* was discovered and selected by the Inventor in July, 2003 in a controlled environment in Apopka, Fla.

Asexual propagation of the new cultivar by tissue culture since July, 2004, in a controlled environment in Apopka, Fla., has shown that the unique features of this new *Colocasia* are stable and reproduced true to type in successive generations.

SUMMARY OF THE INVENTION

The following traits have been repeatedly observed and are determined to be the unique characteristics of 'Midnight'. These characteristics in combination distinguish 'Midnight' as a new and distinct cultivar of *Colocasia:*

1. Tall and upright plant form.
2. Relatively slow growth rate.
3. Uniformly black-colored leaves.

In side-by-side comparisons conducted by the Inventor in Apopka, Fla., plants of the new *Colocasia* differed primarily from plants of the parent selection in leaf color as plants of the parent selection had green and black bi-colored leaves.

Plants of the new *Colocasia* can be compared to plants of the cultivar Black Magic, not patented. In side-by-side comparisons conducted in Apopka, Fla., plants of the new *Colocasia* differed primarily from plants of the *Colocasia* cultivar Black Magic in leaf color as plants of the cultivar Black Magic did not have uniformly black-colored leaves.

BRIEF DESCRIPTION OF THE PHOTOGRAPH

The accompanying colored photograph illustrates the overall appearance of the new *Colocasia,* showing the colors as true as it is reasonably possible to obtain in colored reproductions of this type. Colors in the photograph may differ slightly from the color values cited in the detailed botanical description which accurately describe the colors of the new *Colocasia.* The photograph comprises a side perspective view of a typical plant of 'Midnight' grown in a container.

DETAILED BOTANICAL DESCRIPTION

The cultivar Midnight has not been observed under all possible environmental conditions. The phenotype may vary somewhat with variations in environment such as temperature and light intensity without, however, any variance in genotype. The following observations and measurements describe plants of the new *Colocasia* that were grown in 15-cm containers, in Sebring, Fla., in a polycarbonate-covered greenhouse with light levels about 5,000 foot-candles. During the production of the plants, day temperatures ranged from about 21° C. to about 33° C. and night temperatures ranged from about 10° C. to about 20° C. Plants used for the photographs and description were about seven months from planting. Color references are made to The Royal Horticultural Society Colour Chart, 2001 Edition, except where general terms of ordinary dictionary significance are used.

Botanical classification: *Colocasia esculenta* cultivar Midnight.

Parentage: Naturally-occurring branch mutation of an unnamed selection of *Colocasia esculenta,* not patented.

Propagation:

*Type.*—By tissue culture.

*Time to initiate roots, summer.*—About one week at 29° C.

*Time to initiate roots, winter.*—About two weeks at 20° C.

*Time to produce a rooted plant, summer.*—About 16 weeks at 29° C.

*Time to produce a rooted plant, winter.*—About 20 weeks at 20° C.

*Root description.*—Fine, fibrous and fleshy; proximal, dark purple in color; distal, greenish white in color.

*Rooting habit.*—Moderate branching; dense.

Plant description:

*Plant form.*—Tall and upright plant form; inverted triangle.

*Growth habit.*—Plant size appropriate for 15-cm to 35-cm containers.

*Growth habit.*—Plants are not freely clumping; usually one primary shoot with few or no basal branches.

*Plant height.*—About 55 cm.

*Plant width* (*spread*).—About 65 cm.

*Foliage description.*—Arrangement: Alternate; simple. Length: About 24 cm. Width: About 17 cm. Shape: Ovate. Apex: Acute to cuspidate. Base: Cordate to sagittate; peltate. Margin: Entire; flat or slightly curved downward. Aspect: Flat or somewhat concave between primary veins. Texture, upper and lower surfaces: Smooth, glabrous. Venation pattern: Pinnate. Color: Developing leaves, upper surface: N186A slightly tinged with 147A. Developing leaves, lower surface: Darker than, but closest to N200B slightly tinged with 147A. Fully expanded leaves, upper surface: N186A to 202A. Fully expanded leaves, lower surface: 202B tinged with N187B. Venation, upper surface: N186A to N187A. Venation, lower surface: N186A. Petiole: Length: About 50 cm. Diameter, distal: About 4 cm. Diameter, proximal: About 6 cm. Color: N186A tinged with N187A. Wing length: About 23 cm. Wing diameter: About 1.4 cm. Wing color, outer surface: N186A tinged with N187A. Wing color, inner surface: N186A; towards the base, N187D veined with N187A.

Flower description: Flower development has not been observed on plants of the new *Colocasia.*

Disease/pest resistance: Plants of the new *Colocasia* have not been observed to be resistant to pathogens and pests common to *Colocasia.*

Temperature tolerance: Plants of the new *Colocasia* have been observed to be tolerant to temperatures ranging from about 4° C. to about 40° C.

It is claimed:

1. A new and distinct cultivar of *Colocasia* plant named 'Midnight', as illustrated and described.

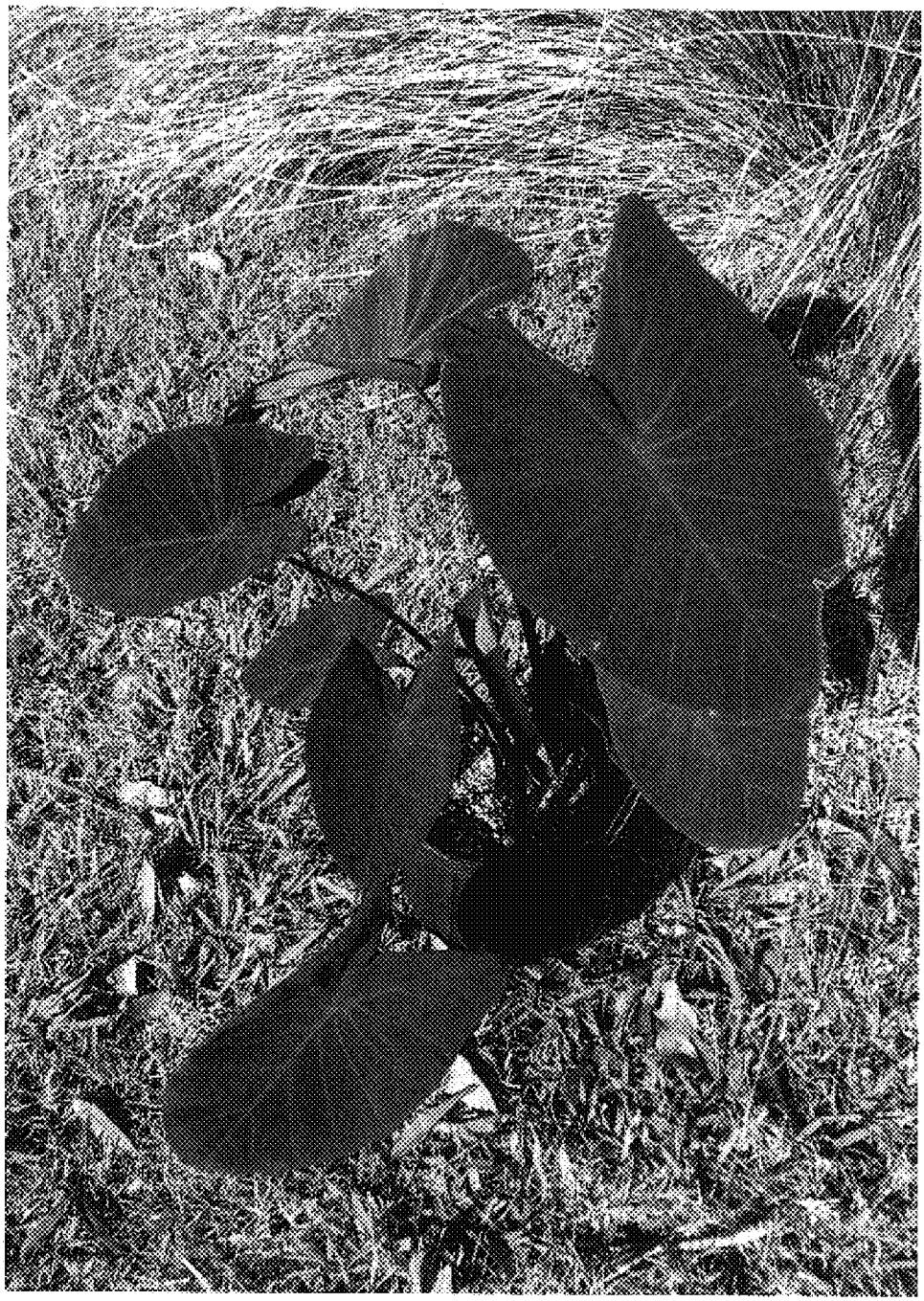

* * * * *